(12) United States Patent
Zhang et al.

(10) Patent No.: US 9,327,022 B2
(45) Date of Patent: May 3, 2016

(54) BSA-SPECIFIC ANTIBODIES

(75) Inventors: Jianbing Zhang, Ottawa (CA); Wangxue Chen, Nepean (CA); C. Roger MacKenzie, Ottawa (CA); Mehdi Arbabi, Ottawa (CA); Shenghua Li, Ottawa (CA)

(73) Assignee: National Research Council of Canada, Ottawa, ON (CA)

( * ) Notice: Subject to any disclaimer, the term of this patent is extended or adjusted under 35 U.S.C. 154(b) by 1358 days.

(21) Appl. No.: 13/124,268

(22) PCT Filed: Oct. 14, 2009

(86) PCT No.: PCT/CA2009/001501
§ 371 (c)(1),
(2), (4) Date: Apr. 14, 2011

(87) PCT Pub. No.: WO2010/043057
PCT Pub. Date: Apr. 22, 2010

(65) Prior Publication Data
US 2011/0282036 A1    Nov. 17, 2011

Related U.S. Application Data

(60) Provisional application No. 61/105,305, filed on Oct. 14, 2008.

(51) Int. Cl.
| | | |
|---|---|---|
| A61K 39/00 | (2006.01) | |
| A61K 39/395 | (2006.01) | |
| C07K 16/00 | (2006.01) | |
| C12P 21/08 | (2006.01) | |
| C07K 16/18 | (2006.01) | |

(52) U.S. Cl.
CPC .............. *A61K 39/395* (2013.01); *C07K 16/18* (2013.01); *A61K 2039/541* (2013.01); *A61K 2039/6037* (2013.01); *A61K 2039/6056* (2013.01); *A61K 2039/645* (2013.01); *C07K 2317/565* (2013.01); *C07K 2317/569* (2013.01); *C07K 2317/92* (2013.01)

(58) Field of Classification Search
None
See application file for complete search history.

(56) References Cited

FOREIGN PATENT DOCUMENTS

| WO | WO03/046560 | 6/2003 |
|---|---|---|
| WO | WO2004/041865 | 5/2004 |
| WO | WO2005/044858 | 5/2005 |
| WO | 2008/096158 | 8/2006 |
| WO | 2008/020079 | 2/2008 |
| WO | 2010/043057 | 4/2010 |
| WO | WO2010/045225 | 4/2010 |

OTHER PUBLICATIONS

Peen et al. 'Amphipathic variable region heavy chain peptides derived from monoclonal human Wegener's anti-PR3 antibodies stimulate lymphocytes from patients with Wegener's granulomatosis and microscopic polyangiitis.' Clin. Exp. Immunol. 125:323-331, 2001.*
Muyldermans et al. 'Nanobodies: Natural Single-Domain Antibodies.' Annu. Rev. Biochem. 82:775-797, 2013.*
De Kruif, J. & Logtenberg, T. Leucine zipper dimerized bivalent and bispecific scFv antibodies from a semi-synthetic antibody phage display library. J Biol Chern 271, 7630-7634 (1996).
Hamers-Casterman, C. et al. Naturally occurring antibodies devoid of light chains. Nature 363, 446-448 (1993).
Jaspers, L., Schon, 0., Famm, K. & Winter, G. Aggregation-resistant domain antibodies selected on phage by heat denaturation. Nat Biotechnol 22, 1161-1165 (2004).
Merritt, E.A. & Hoi, W.G. AB5 toxins. Current opinion in structural biology 5, 165-171 (1995).
Nielsen, U.B., Adams, G.P., Weiner, L.M. & Marks, J.D. Targeting of bivalent anti• ErbB2 diabody antibody fragments to tumor cells is independent of the intrinsic antibody affinity. Cancer research 60, 6434-6440 (2000).
Nuttall, S.D. et al. Isolation and characterization of an IgNAR variable domain specific for the human mitochondrial translocase receptor Tom70. European journal of biochemistry I FEBS 270, 3543-3554 (2003).
Padlan, E.A. Anatomy of the antibody molecule. Molecular immunology 31, 169-217 (1994).
Ridgway, J.B., Presta, L.G. & Carter, P. 'Knobs-into-holes' engineering of antibody CH3 domains for heavy chain heterodimerization. Protein Eng 9, 617-621 (1996).
Tijink, Bernard M., et al., Improved tumor targeting of anti-epidermal growth factor receptor Nanobodies through albumin binding: taking advantage of modular Nanobody technology, Mol. Cancer. Ther 7(8), pp. 2288-2297 (2008).
To, R. et al. Isolation of monomeric human V(H)s by a phage selection. J Biol Chern 280, 41395-41403 (2005).
Zhang, J. et al. A pentavalent single-domain antibody approach to tumor antigen discovery and the development of novel proteomics reagents. J Mol Biol 341, 161-169 (2004).
Zhang, J. et al. Pentamerization of single-domain antibodies from phage libraries: a novel strategy for the rapid generation of high-avidity antibody reagents. J Mol Biol 335, 49-56 (2004).
Extended European Search Report issued Jan. 3, 2014 for corresponding EP Appln No. 13190416.1.

* cited by examiner

*Primary Examiner* — Nora Rooney
(74) *Attorney, Agent, or Firm* — Sonia Patenaude

(57) ABSTRACT

The invention relates to antibodies specific to serum albumins. More specifically, the invention relates to camelid single domain antibodies and pentabodies binding to serum albumins of various species with various affinities.

14 Claims, 6 Drawing Sheets

A

```
BSA7   QVQLVESGGGLVQAGGSLRLSCATSERTAISYYAMGWFCQAPG
BSA8   QVKLEESGGGLAQAGGSLRLSCAASERT-FIRYTIGWFRQAPG
BSA12  QVKLEESGGGLVQVGDSLRLSCAASGRT-FSNYTMAWFRQFPG
BSA16  QVKLEESGGGLVQAGGSLRLSCAPSGRT-FRTWRMGWFRQAPG

BSA7   EERDFVAAINWSGETTKYADSVKGRFTISRDHAKNTVYLQMNN
BSA8   KEREFVGRVNWSGGDTYYADSVKGRFTISRDNAKTTVTLQMSS
BSA12  KEREFVAVVSRGGATDYADSVKGRFTISRDNAKNTMYLQMNS
BSA16  KEREFVAAINLNTGNTYYVDSVKGRFTISGDYAKNTLYLQMNS

BSA7   LKPEDTAVYYCAAGAR---FDDIGS--YDYWGQGTQVTVSS
BSA8   LKPEDTAVYSCAASPKWSE-IP---REYIYWGPGTQVTVSS
BSA12  LKTEDTAVYYCAAGTDLSYY--YSTKKWAYWGQGTQVTVSS
BSA16  LKPEDTAVYFCAARSPDSDYVPLSSIDYQYWGQGTQVTVSS
```

B

```
[ompA] [    sdAb    ] [myc] [H]

[ompA] [ CTB ] [L] [  sdAb  ] [myc] [H]
```

| | | |
|---|---|---|
| ompA | signal sequence | MKKTAIAIAVALAGFATVAQA |
| CTB | Cholera toxin B subunit | AAP72183, AA2-104 |
| L | Linker | GGGGSGGGGSGGGGS |
| sdAb | BSA8, BSA12 or BSA16 | |
| myc | c-Myc detection tag | GSEQKLISEEDLN |
| H | 6XHis purification tag | HHHHHH |

FIG. 1

SEQUENCE LISTING

<160> NUMBER OF SEQ ID NOS: 21

<210> SEQ ID NO 1
<211> LENGTH: 5
<212> TYPE: PRT
<213> ORGANISM: Artificial Sequence
<220> FEATURE:
<223> OTHER INFORMATION: CDR1 BSA8

<400> SEQUENCE: 1

Asn Tyr Thr Met Ala
1               5

<210> SEQ ID NO 2
<211> LENGTH: 5
<212> TYPE: PRT
<213> ORGANISM: Artificial Sequence
<220> FEATURE:
<223> OTHER INFORMATION: CDR1 BSA12

<400> SEQUENCE: 2

Arg Tyr Thr Ile Gly
1               5

<210> SEQ ID NO 3
<211> LENGTH: 5
<212> TYPE: PRT
<213> ORGANISM: Artificial Sequence
<220> FEATURE:
<223> OTHER INFORMATION: CDR1 BSA16

<400> SEQUENCE: 3

Thr Trp Arg Met Gly
1               5

<210> SEQ ID NO 4
<211> LENGTH: 17
<212> TYPE: PRT
<213> ORGANISM: Artificial Sequence
<220> FEATURE:
<223> OTHER INFORMATION: CDR2 BSA8

<400> SEQUENCE: 4

Val Val Ser Arg Gly Gly Gly Ala Thr Asp Tyr Ala Asp Ser Val Lys
1               5                   10                  15

Gly

<210> SEQ ID NO 5
<211> LENGTH: 17
<212> TYPE: PRT
<213> ORGANISM: Artificial Sequence
<220> FEATURE:
<223> OTHER INFORMATION: CDR2 BSA12

<400> SEQUENCE: 5

Arg Val Asn Trp Ser Gly Gly Asp Thr Tyr Tyr Ala Asp Ser Val Lys
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: CDR2 BSA16

```
<400> SEQUENCE: 6

Ala Ile Asn Leu Asn Thr Gly Asn Thr Tyr Tyr Val Asp Ser Val Lys
1               5                   10                  15

Gly

<210> SEQ ID NO 7
<211> LENGTH: 15
<212> TYPE: PRT
<213> ORGANISM: Artificial Sequence
<220> FEATURE:
<223> OTHER INFORMATION: CDR3 BSA8

<400> SEQUENCE: 7

Gly Thr Asp Leu Ser Tyr Tyr Tyr Ser Thr Lys Lys Trp Ala Tyr
1               5                   10                  15

<210> SEQ ID NO 8
<211> LENGTH: 13
<212> TYPE: PRT
<213> ORGANISM: Artificial Sequence
<220> FEATURE:
<223> OTHER INFORMATION: CDR3 BSA12

<400> SEQUENCE: 8

Ser Pro Lys Trp Ser Glu Ile Pro Arg Glu Tyr Ile Tyr
1               5                   10

<210> SEQ ID NO 9
<211> LENGTH: 17
<212> TYPE: PRT
<213> ORGANISM: Artificial Sequence
<220> FEATURE:
<223> OTHER INFORMATION: CDR3 BSA16

<400> SEQUENCE: 9

Arg Ser Pro Asp Ser Asp Tyr Val Pro Leu Ser Ser Ile Asp Tyr Gln
1               5                   10                  15

Tyr

<210> SEQ ID NO 10
<211> LENGTH: 122
<212> TYPE: PRT
<213> ORGANISM: Artificial Sequence
<220> FEATURE:
<223> OTHER INFORMATION: BSA7

<400> SEQUENCE: 10

Gln Val Gln Leu Val Glu Ser Gly Gly Gly Leu Val Gln Ala Gly Gly
1               5                   10                  15

Ser Leu Arg Leu Ser Cys Ala Thr Ser Glu Arg Thr Ala Ile Ser Tyr
            20                  25                  30

Tyr Ala Met Gly Trp Phe Cys Gln Ala Pro Gly Glu Glu Arg Asp Phe
        35                  40                  45

Val Ala Ala Ile Asn Trp Ser Gly Glu Thr Thr Lys Tyr Ala Asp Ser
    50                  55                  60

Val Lys Gly Arg Phe Thr Ile Ser Arg Asp His Ala Lys Asn Thr Val
65                  70                  75                  80

Tyr Leu Gln Met Asn Asn Leu Lys Pro Glu Asp Thr Ala Val Tyr Tyr
                85                  90                  95

Cys Ala Ala Gly Ala Arg Phe Asp Ile Gly Ser Tyr Asp Tyr Trp
            100                 105                 110
```

-continued

```
Gly Gln Gly Thr Gln Val Thr Val Ser Ser
        115                 120
```

<210> SEQ ID NO 11
<211> LENGTH: 122
<212> TYPE: PRT
<213> ORGANISM: Artificial Sequence
<220> FEATURE:
<223> OTHER INFORMATION: BSA8

<400> SEQUENCE: 11

```
Gln Val Lys Leu Glu Glu Ser Gly Gly Gly Leu Ala Gln Ala Gly Gly
1               5                   10                  15

Ser Leu Arg Leu Ser Cys Ala Ala Ser Glu Arg Thr Phe Ile Arg Tyr
            20                  25                  30

Thr Ile Gly Trp Phe Arg Gln Ala Pro Gly Lys Glu Arg Glu Phe Val
        35                  40                  45

Gly Arg Val Asn Trp Ser Gly Gly Asp Thr Tyr Tyr Ala Asp Ser Val
    50                  55                  60

Lys Gly Arg Phe Thr Ile Ser Arg Asp Asn Ala Lys Thr Thr Val Thr
65                  70                  75                  80

Leu Gln Met Ser Ser Leu Lys Pro Glu Asp Thr Ala Val Tyr Ser Cys
                85                  90                  95

Ala Ala Ser Pro Lys Trp Ser Glu Ile Pro Arg Glu Tyr Ile Tyr Trp
            100                 105                 110

Gly Pro Gly Thr Gln Val Thr Val Ser Ser
        115                 120
```

<210> SEQ ID NO 12
<211> LENGTH: 123
<212> TYPE: PRT
<213> ORGANISM: Artificial Sequence
<220> FEATURE:
<223> OTHER INFORMATION: BSA12

<400> SEQUENCE: 12

```
Gln Val Lys Leu Glu Glu Ser Gly Gly Gly Leu Val Gln Val Gly Asp
1               5                   10                  15

Ser Leu Arg Leu Ser Cys Ala Ala Ser Gly Arg Thr Phe Ser Asn Tyr
            20                  25                  30

Thr Met Ala Trp Phe Arg Gln Phe Pro Gly Lys Glu Arg Glu Phe Val
        35                  40                  45

Ala Val Val Ser Arg Gly Gly Gly Ala Thr Asp Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Thr Asp Thr Ala Val Tyr Tyr Cys Ala
                85                  90                  95

Ala Gly Thr Asp Leu Ser Tyr Tyr Tyr Ser Thr Lys Lys Trp Ala Tyr
            100                 105                 110

Trp Gly Gln Gly Thr Gln Val Thr Val Ser Ser
        115                 120
```

<210> SEQ ID NO 13
<211> LENGTH: 126
<212> TYPE: PRT
<213> ORGANISM: Artificial Sequence
<220> FEATURE:
<223> OTHER INFORMATION: BSA16

<400> SEQUENCE: 13

```
Gln Val Lys Leu Glu Glu Ser Gly Gly Gly Leu Val Gln Ala Gly Gly
 1               5                  10                  15
Ser Leu Arg Leu Ser Cys Ala Pro Ser Gly Arg Thr Phe Arg Thr Trp
            20                  25                  30
Arg Met Gly Trp Phe Arg Gln Ala Pro Gly Lys Glu Arg Glu Phe Val
        35                  40                  45
Ala Ala Ile Asn Leu Asn Thr Gly Asn Thr Tyr Tyr Val Asp Ser Val
    50                  55                  60
Lys Gly Arg Phe Thr Ile Ser Gly Asp Tyr Ala Lys Asn Thr Leu Tyr
65                  70                  75                  80
Leu Gln Met Asn Ser Leu Lys Pro Glu Asp Thr Ala Val Tyr Phe Cys
                85                  90                  95
Ala Ala Arg Ser Pro Asp Ser Asp Tyr Val Pro Leu Ser Ile Asp
            100                 105                 110
Tyr Gln Tyr Trp Gly Gln Gly Thr Gln Val Thr Val Ser Ser
            115                 120                 125
```

<210> SEQ ID NO 14
<211> LENGTH: 240
<212> TYPE: PRT
<213> ORGANISM: Artificial Sequence
<220> FEATURE:
<223> OTHER INFORMATION: BSA8 PENTAMER (NOT INCLUDING OMPA OR CMYC)

<400> SEQUENCE: 14

```
Thr Pro Gln Asn Ile Thr Asp Leu Cys Ala Glu Tyr His Asn Thr Gln
 1               5                  10                  15
Ile Tyr Thr Leu Asn Asp Lys Ile Asp Ser Tyr Thr Glu Ser Leu Ala
            20                  25                  30
Gly Lys Arg Glu Met Ala Ile Ile Thr Phe Lys Asn Gly Ala Ile Phe
        35                  40                  45
Gln Val Glu Val Pro Gly Ser Gln His Ile Asp Ser Gln Lys Lys Ala
    50                  55                  60
Ile Glu Arg Met Lys Asp Thr Leu Arg Ile Ala Tyr Leu Thr Glu Ala
65                  70                  75                  80
Lys Val Glu Lys Leu Cys Val Trp Asn Asn Lys Thr Pro His Ala Ile
                85                  90                  95
Ala Ala Ile Ser Met Ala Asn Gly Gly Gly Ser Gly Gly Gly Gly
            100                 105                 110
Ser Gly Gly Gly Gly Ser Gln Val Lys Leu Glu Glu Ser Gly Gly Gly
            115                 120                 125
Leu Ala Gln Ala Gly Gly Ser Leu Arg Leu Ser Cys Ala Ala Ser Glu
    130                 135                 140
Arg Thr Phe Ile Arg Tyr Thr Ile Gly Trp Phe Arg Gln Ala Pro Gly
145                 150                 155                 160
Lys Glu Arg Glu Phe Val Gly Arg Val Asn Trp Ser Gly Gly Asp Thr
                165                 170                 175
Tyr Tyr Ala Asp Ser Val Lys Gly Arg Phe Thr Ile Ser Arg Asp Asn
            180                 185                 190
Ala Lys Thr Thr Val Thr Leu Gln Met Ser Ser Leu Lys Pro Glu Asp
        195                 200                 205
Thr Ala Val Tyr Ser Cys Ala Ala Ser Pro Lys Trp Ser Glu Ile Pro
    210                 215                 220
Arg Glu Tyr Ile Tyr Trp Gly Pro Gly Thr Gln Val Thr Val Ser Ser
```

<210> SEQ ID NO 15
<211> LENGTH: 241
<212> TYPE: PRT
<213> ORGANISM: Artificial Sequence
<220> FEATURE:
<223> OTHER INFORMATION: BSA12 PENTAMER (NOT INCLUDING OMPA or CMYC)

<400> SEQUENCE: 15

Thr Pro Gln Asn Ile Thr Asp Leu Cys Ala Glu Tyr His Asn Thr Gln
1               5                   10                  15

Ile Tyr Thr Leu Asn Asp Lys Ile Asp Ser Tyr Thr Glu Ser Leu Ala
            20                  25                  30

Gly Lys Arg Glu Met Ala Ile Ile Thr Phe Lys Asn Gly Ala Ile Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn Gly Gly Gly Ser Gly Gly Gly Gly
            100                 105                 110

Ser Gly Gly Gly Gly Ser Gln Val Lys Leu Glu Glu Ser Gly Gly Gly
        115                 120                 125

Leu Val Gln Val Gly Asp Ser Leu Arg Leu Ser Cys Ala Ala Ser Gly
    130                 135                 140

Arg Thr Phe Ser Asn Tyr Thr Met Ala Trp Phe Arg Gln Phe Pro Gly
145                 150                 155                 160

Lys Glu Arg Glu Phe Val Ala Val Val Ser Arg Gly Gly Gly Ala Thr
                165                 170                 175

Asp Tyr Ala Asp Ser Val Lys Gly Arg Phe Thr Ile Ser Arg Asp Asn
            180                 185                 190

Ala Lys Asn Thr Met Tyr Leu Gln Met Asn Ser Leu Lys Thr Asp Thr
        195                 200                 205

Ala Val Tyr Tyr Cys Ala Ala Gly Thr Asp Leu Ser Tyr Tyr Tyr Ser
    210                 215                 220

Thr Lys Lys Trp Ala Tyr Trp Gly Gln Gly Thr Gln Val Thr Val Ser
225                 230                 235                 240

Ser

<210> SEQ ID NO 16
<211> LENGTH: 244
<212> TYPE: PRT
<213> ORGANISM: Artificial Sequence
<220> FEATURE:
<223> OTHER INFORMATION: BSA16 PENTAMER (NOT INCLUDING OMPA or CMYC)

<400> SEQUENCE: 16

Thr Pro Gln Asn Ile Thr Asp Leu Cys Ala Glu Tyr His Asn Thr Gln
1               5                   10                  15

Ile Tyr Thr Leu Asn Asp Lys Ile Asp Ser Tyr Thr Glu Ser Leu Ala
            20                  25                  30

Gly Lys Arg Glu Met Ala Ile Ile Thr Phe Lys Asn Gly Ala Ile Phe
        35                  40                  45

Gln Val Glu Val Pro Gly Ser Gln His Ile Asp Ser Gln Lys Lys Ala

```
                50                   55                  60
Ile Glu Arg Met Lys Asp Thr Leu Arg Ile Ala Tyr Leu Thr Glu Ala
 65                  70                  75                  80

Lys Val Glu Lys Leu Cys Val Trp Asn Asn Lys Thr Pro His Ala Ile
                 85                  90                  95

Ala Ala Ile Ser Met Ala Asn Gly Gly Gly Ser Gly Gly Gly
            100                 105                 110

Ser Gly Gly Gly Gly Ser Gln Val Lys Leu Glu Glu Ser Gly Gly Gly
            115                 120                 125

Leu Val Gln Ala Gly Gly Ser Leu Arg Leu Ser Cys Ala Pro Ser Gly
            130                 135                 140

Arg Thr Phe Arg Thr Trp Arg Met Gly Trp Phe Arg Gln Ala Pro Gly
145                 150                 155                 160

Lys Glu Arg Glu Phe Val Ala Ala Ile Asn Leu Asn Thr Gly Asn Thr
                165                 170                 175

Tyr Tyr Val Asp Ser Val Lys Gly Arg Phe Thr Ile Ser Gly Asp Tyr
            180                 185                 190

Ala Lys Asn Thr Leu Tyr Leu Gln Met Asn Ser Leu Lys Pro Glu Asp
            195                 200                 205

Thr Ala Val Tyr Phe Cys Ala Ala Arg Ser Pro Asp Ser Asp Tyr Val
            210                 215                 220

Pro Leu Ser Ser Ile Asp Tyr Gln Tyr Trp Gly Gln Gly Thr Gln Val
225                 230                 235                 240

Thr Val Ser Ser
```

<210> SEQ ID NO 17
<211> LENGTH: 21
<212> TYPE: PRT
<213> ORGANISM: Artificial Sequence
<220> FEATURE:
<223> OTHER INFORMATION: OMPA

<400> SEQUENCE: 17

```
Met Lys Lys Thr Ala Ile Ala Ile Ala Val Ala Leu Ala Gly Phe Ala
 1               5                  10                  15

Thr Val Ala Gln Ala
             20
```

<210> SEQ ID NO 18
<211> LENGTH: 15
<212> TYPE: PRT
<213> ORGANISM: Artificial Sequence
<220> FEATURE:
<223> OTHER INFORMATION: LINKER

<400> SEQUENCE: 18

```
Gly Gly Gly Gly Ser Gly Gly Gly Gly Ser Gly Gly Gly Gly Ser
 1               5                  10                  15
```

<210> SEQ ID NO 19
<211> LENGTH: 13
<212> TYPE: PRT
<213> ORGANISM: Artificial Sequence
<220> FEATURE:
<223> OTHER INFORMATION: CMYC

<400> SEQUENCE: 19

```
Gly Ser Glu Gln Lys Leu Ile Ser Glu Glu Asp Leu Asn
 1               5                  10
```

<210> SEQ ID NO 20
<211> LENGTH: 6
<212> TYPE: PRT
<213> ORGANISM: Artificial Sequence
<220> FEATURE:
<223> OTHER INFORMATION: HISTIDINE TAG

<400> SEQUENCE: 20

His His His His His His
1               5

<210> SEQ ID NO 21
<211> LENGTH: 103
<212> TYPE: PRT
<213> ORGANISM: Artificial Sequence
<220> FEATURE:
<223> OTHER INFORMATION: CTB

<400> SEQUENCE: 21

Thr Pro Gln Asn Ile Thr Asp Leu Cys Ala Glu Tyr His Asn Thr Gln
1               5                   10                  15

Ile Tyr Thr Leu Asn Asp Lys Ile Asp Ser Tyr Thr Glu Ser Leu Ala
                20                  25                  30

Gly Lys Arg Glu Met Ala Ile Ile Thr Phe Lys Asn Gly Ala Ile Phe
            35                  40                  45

Gln Val Glu Val Pro Gly Ser Gln His Ile Asp Ser Gln Lys Lys Ala
        50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn
                100

BSA-SPECIFIC ANTIBODIES

CROSS-REFERENCE TO RELATED APPLICATIONS

This application is a national phase entry of International Patent Application PCT/CA2009/001501 filed Oct. 14, 2009, which claims the benefit of U.S. Provisional Patent Application Ser. No. 61/105,305 filed Oct. 14, 2008.

FIELD OF THE INVENTION

The present invention relates to BSA-specific antibodies. More specifically, the invention relates to BSA-specific antibody fragments.

BACKGROUND OF THE INVENTION

Antibodies play an important role in diagnostic and clinical applications for neutralizing and identifying pathogens. As is known in the art, interaction of the heavy and light chain variable domains ($V_H$ and $V_L$) of antibodies, comprising three complementarity-determining regions (CDRs) each, results in the formation of an antigen binding region (Fv). The variable region of an antibody contains the antigen binding determinants of the molecule, and thus determines the specificity of an antibody for its target antigen. This characteristic structure of antibodies provides a stable scaffold upon which substantial antigen-binding diversity can be explored by the immune system to obtain specificity for a broad array of antigens.

The immune repertoire of camelids (camels, dromedaries and llamas) is unique in that it possesses unusual types of antibodies referred to as heavy-chain antibodies (Hamers et al, 1993). These antibodies lack light chains and thus their combining sites consist of one domain, termed $V_HH$. Single domain antibodies (sdAbs) have also been observed in shark and are termed VNARs. Furthermore, recombinant sdAbs may also be prepared using knowledge gleaned from structural studies of naturally-occurring sdAbs.

sdAbs provide several advantages over single-chain Fv (scFv) fragments derived from conventional four-chain antibodies. Single domain antibodies are comparable to their scFv counterparts in terms of affinity, but outperform scFvs in terms of solubility, stability, resistance to aggregation, refoldability, expression yield, and ease of DNA manipulation, library construction and 3-D structural determinations. Many of the aforementioned properties of sdAbs are desired in applications involving antibodies.

Naturally-occurring single domain antibodies can be isolated from libraries (for example, phage display libraries) by panning based solely upon binding property as the selection criterion (Arbabi-Ghahroudi et al., 1997; Lauwereys et al., 1998). However, antibodies/peptides isolated with this method usually have a low to moderate affinity to their antigens/ligands. Since each M13 phage particle presents five copies of the minor coat protein pill, a phage particle displaying an antibody fragment on all copies of pill can be considered a pentavalent antibody. This multivalent display of antibody fragments on phage greatly increases the avidity of the antibody and facilitates both screening and evaluation of phage antibodies. Isolated antibody fragments (scFvs or sdAbs) or peptides bind antigen much less efficiently since they exist primarily in a monovalent form and lack avidity.

An antibody fragment oligomerization strategy that permits pentavalency as in pill phage display is the subject of PCT/CA02/01829 (MacKenzie and Zhang). Fusion of a single domain antibody (sdAb) to the homo-pentamerization domain of the B subunit of verotoxin (VT1B) results in the simultaneous pentamerization of the sdAb. The pentavalent sdAbs, termed pentabodies, bind much more strongly to immobilized antigen than their monomeric counterparts. In the instance of peptide hormone-binding sdAb, pentamerization resulted in $10^3$ to $10^4$-fold improvement in binding to immobilized antigen.

Thus, there is a need in the art to isolate sdAbs that are antigen-specific, soluble and structurally stable for use in clinical and diagnostic applications.

SUMMARY OF THE INVENTION

The present invention relates to BSA-specific antibodies. More specifically, the invention relates to BSA-specific antibody fragments.

The present invention provides an isolated or purified antibody or fragment thereof specific to serum albumin, comprising the sequence of complementarity determining region (CDR) 1 selected from sequences NYTMA (SEQ ID NO: 1), RYTIG (SEQ ID NO: 2), and TWRMG (SEQ ID NO: 3);

the sequence of CDR2 selected from sequences VVSRGG-GATDYADSVKG (SEQ ID NO: 4), RVNWSGGD-TYYADSVKG (SEQ ID NO: 5), and AINLNTGN-TYYVDSVKG (SEQ ID NO: 6); and the sequence of CDR3 selected from sequences GTDL-SYYYSTKKWAY (SEQ ID NO: 7), SPK-WSEIPREYIY (SEQ ID NO: 8), and RSPDSDYV-PLSSIDYQY (SEQ ID NO: 9).

The isolated or purified antibody or fragment thereof may be a single-domain antibody (sdAb); the sdAb may be of camelid origin.

The isolated or purified antibody or fragment thereof of the present invention may comprise the sequence:

```
(SEQ ID NO: 11; also referred to herein as BSA8)
QVKLEESGGGLAQAGGSLRLSCAASERTFIRYTIGWFRQAPGKEREFVG

RVNWSGGDTYYADSVKGRFTISRDNAKTTVTLQMSSLKPEDTAVYSCAA

SPKWSEIPREYIYWGPGTQVTVSS,
``` or a sequence substantially identical thereto. Alternatively, the isolated or purified antibody or fragment thereof may comprise the sequence:

```
(SEQ ID NO: 12; also referred to herein as BSA12)
QVKLEESGGGLVQVGDSLRLSCAASGRTFSNYTMAWFRQFPGKEREFVA

VVSRGGGATDYADSVKGRFTISRDNAKNTMYLQMNSLKTDTAVYYCAAG

TDLSYYYSTKKWAYWGQGTQVTVSS
``` or a sequence substantially identical thereto. In yet another alternative, the isolated or purified antibody or fragment thereof may comprise the sequence:

```
(SEQ ID NO: 13; also referred to herein as BSA16)
QVKLEESGGGLVQAGGSLRLSCAPSGRTFRTWRMGWFRQAPGKEREFVA

AINLNTGNTYYVDSVKGRFTISGDYAKNTLYLQMNSLKPEDTAVYFCAA

RSPDSDYVPLSSIDYQYWGQGTQVTVSS,
``` or a sequence substantially identical thereto.

The isolated or purified antibody or fragment thereof of the present invention may possess a dissociation constant to its ligand lower than $10^{-6}$ M; alternatively, the dissociation constant may be lower than $10^{-7}$ M; or, the dissociation constant of the antibody or fragment thereof may be lower than $10^{-11}$ M.

The present invention also provides an isolated or purified antibody or fragment thereof as described above, wherein the antibody or fragment thereof is in a multivalent display. The antibody or fragment thereof may be a pentamer. In one embodiment, at least one subunit of the pentamer comprises a sequence selected from SEQ ID NO: 14, SEQ ID NO: 15, SEQ ID NO: 16 or a substantially identical sequence thereto.

The present invention further provides a nucleic acid molecule and/or a vector encoding the isolated or purified antibody or fragment thereof as described herein.

In accordance with the present invention, there is also provided an isolated or purified antibody or fragment thereof as described, wherein the antibody or fragment thereof is immobilized onto a surface. The surface may be a microtiter plate, a sensorchip, or a chromatography resin.

Additional aspects and advantages of the present invention will be apparent in view of the following description. The detailed description and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

These and other features of the invention will now be described by way of example, with reference to the appended drawings, wherein.

DETAILED DESCRIPTION OF THE INVENTION

Figure 1:
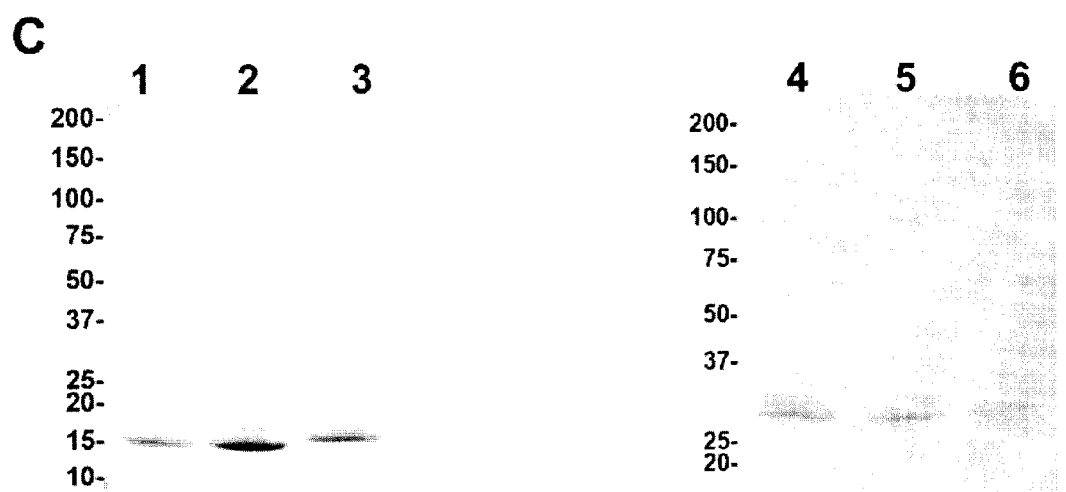
FIG. 1 shows the sdAbs and CTB-based pentabodies constructed in this work. (A) Sequences of BSA7 (SEQ ID NO: 10), BSA8 (SEQ ID NO: 11), BSA12 (SEQ ID NO: 12), and BSA16 (SEQ ID NO: 13) with the three complementarity determining regions underlined. (B) Schematic drawing of primary structure of the sdAbs and their pentabodies. The ompA signal peptide (SEQ ID NO: 17) will be removed during the secretion of the protein. CTB (SEQ ID NO: 21) and the sdAbs are linked by a 15 amino acid linker (L; SEQ ID NO: 18) and tagged with a c-Myc detection tag (myc; SEQ ID NO: 19) and a 6× histidine purification tag (SEQ ID NO: 20). (C) SDS-PAGE of purified BSA8, BSA12, BSA16, C3C-BSA8, C3C-BSA12, and C3C-BSA16 (lane 1-6).

The present invention relates to BSA-specific antibodies. More specifically, the invention relates to BSA-specific antibody fragments.

In one embodiment, the present invention provides an isolated or purified antibody or fragment thereof specific to serum albumin, comprising
  the sequence of complementarity determining region (CDR) 1 is selected from sequences NYTMA (SEQ ID NO: 1), RYTIG (SEQ ID NO: 2), and TWRMG (SEQ ID NO: 3);
  the sequence of CDR2 is selected from sequences VVS-RGGGATDYADSVKG (SEQ ID NO: 4), RVNWSG-GDTYYADSVKG (SEQ ID NO: 5), and AINLNTGN-TYYVDSVKG (SEQ ID NO: 6); and
  the sequence of CDR3 is selected from sequences GTDL-SYYYSTKKWAY (SEQ ID NO: 7), SPK-WSEIPREYIY (SEQ ID NO: 8), and RSPDSDYV-PLSSIDYQY (SEQ ID NO: 9).

The term "antibody", also referred to in the art as "immunoglobulin" (Ig), used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable ($V_L$) and a constant ($C_L$) domain, while the heavy chain folds into a variable ($V_H$) and three constant ($C_H$, $C_{H2}$, $C_{H3}$) domains. Interaction of the heavy and light chain variable domains ($V_H$ and $V_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen binding determinants of the molecule, and thus determines the specificity of an antibody for its target antigen. The majority of sequence variability occurs in the "complementarity-determining regions" (CDRs). There are six CDRs total, three each per variable heavy and light chain; the CDR combine to form the antigen-binding site, and contribute to binding and recognition of an antigenic determinant. The region outside of the CDRs is referred to as the framework region (FR). This characteristic structure of antibodies provides a stable scaffold upon which substantial antigen-binding diversity can be explored by the immune system to obtain specificity for a broad array of antigens[1].

An "antibody fragment" as referred to herein may include any suitable antigen-binding antibody fragment known in the art. The antibody fragment may be obtained by manipulation of a naturally-occurring antibody, or may be obtained using recombinant methods. For example, an antibody fragment may include, but is not limited to Fv, single-chain Fv (scFV; a molecule consisting $V_L$ and $V_H$ connected with a peptide linker), Fab, Fab$_2$, single domain antibody (sdAb), and multivalent presentations of these.

The antibody fragment may be a single domain antibody (sdAb), which is derived from heavy chain antibodies of camelid origin[2]. These antibodies lack light chains and thus their antigen binding sites consist of one domain, termed $V_H H$. sdAbs have also been observed in shark and are termed VNARs[3], and may be engineered based on human heavy chain sequences[4,5]. As used herein, sdAb includes those directly isolated from $V_H$, $V_H H$ or $V_{NAR}$ reservoir of any origin through phage display or other display technologies and those generated through further modification of such sdAbs by humanization, affinity maturation, stablization and other way of antibody engineering. The term also includes homologues, derivatives, or fragments that are capable of functioning as a single-domain antibody domain.

A person of skill in the art would be well-acquainted with the structure of a single-domain antibody (see, for example, 3DWT, 2P42 in protein data bank). Most notably, an sdAb comprises a single immunoglobulin domain, therefore only three CDRs form the antigen-binding site. However, not all CDRs may be required for binding the antigen. For example, and without wishing to be limiting, one, two, or three of the CDRs may contribute to binding and recognition of the antigen by the sdAb of the present invention. The CDRs of the sdAb are referred to herein as CDR1, CDR2, and CDR3.

By "specific to serum albumin", it is meant that the antibody or fragment thereof of the present invention recognizes and binds to one or more than one serum albumin from various sources including, but not limited to bovine, human, murine, porcine, sheep, canine, goat, guinea pig, rabbit, or ovalbumin. In a specific, non-limiting example, the antibody or fragment thereof of the present invention recognizes and binds to bovine serum albumin (BSA).

In one non-limiting embodiment, the antibody or fragment thereof may have a CDR1 of sequence NYTMA (SEQ ID NO: 1), RYTIG (SEQ ID NO: 2), or TWRMG (SEQ ID NO: 3); CDR2 of sequence VVSRGGGATDYADSVKG (SEQ ID NO: 4), RVNWSGGDTYYADSVKG (SEQ ID NO: 5), or AINLNTGNTYYVDSVKG (SEQ ID NO: 6); and CDR3 of sequence GTDLSYYYSTKKWAY (SEQ ID NO: 7), SPKWSEIPREYIY (SEQ ID NO: 8), or RSPDSDYVPLSSIDYQY (SEQ ID NO: 9). The antibody or fragment thereof may be an sdAb. The sdAb may be of camelid origin, and thus may be based on camelid framework regions; alternatively, the CDR may be grafted onto VNAR or human $V_H H$ framework regions.

In a specific, non-limiting example, the antibody or fragment thereof may comprise the sequence:

```
(SEQ ID NO: 11, also referred to herein as BSA8),
QVKLEESGGGLAQAGGSLRLSCAASERTFIRYTIGWFRQAPGKEREFVG

RVNWSGGDTYYADSVKGRFTISRDNAKTTVTLQMSSLKPEDTAVYSCAA

SPKWSEIPREYIYWGPGTQVTVSS,
``` or a sequence substantially identical thereto.

In another example, the sequence of the antibody or fragment thereof may comprise the sequence:

```
(SEQ ID NO: 12; also referred to herein as BSA12)
QVKLEESGGGLVQVGDSLRLSCAASGRTFSNYTMAWFRQFPGKEREFVA

VVSRGGGATDYADSVKGRFTISRDNAKNTMYLQMNSLKTDTAVYYCAAG

TDLSYYYSTKKWAYWGQGTQVTVSS,
``` or a sequence substantially identical thereto.

In yet another example, the sequence of the antibody or fragment thereof may comprise the sequence:

```
(SEQ ID NO: 13; also referred to herein as BSA16)
QVKLEESGGGLVQAGGSLRLSCAPSGRTFRTWRMGWFRQAPGKEREFVA

AINLNTGNTYYVDSVKGRFTISGDYAKNTLYLQMNSLKPEDTAVYFCAA

RSPDSDYVPLSSIDYQYWGQGTQVTVSS,
``` or a sequence substantially identical thereto.

A substantially identical sequence may comprise one or more conservative amino acid mutations. It is known in the art that one or more conservative amino acid mutations to a reference sequence may yield a mutant peptide with no substantial change in physiological, chemical, or functional properties compared to the reference sequence; in such a case, the reference and mutant sequences would be considered "substantially identical" polypeptides. Conservative amino acid mutation may include addition, deletion, or substitution of an amino acid; a conservative amino acid substitution is defined herein as the substitution of an amino acid residue for another amino acid residue with similar chemical properties (e.g. size, charge, or polarity).

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at http://ca.expasy.org/tools/blast/), BLAST-P, Blast-N, or FASTA-N, or any other appropriate software that is known in the art.

The substantially identical sequences of the present invention may be at least 75% identical; in another example, the substantially identical sequences may be at least 70, 71, 72, 73, 74, 75, 80, 85, 90, 95, or 100% identical at the amino acid level to sequences described herein. Importantly, the substantially identical sequences retain the activity and specificity of the reference sequence.

By way of example only, and without limiting the scope of the invention, the percent identity between BSA8 and BSA12 is 71%; between BSA8 and BSA16 is 74%; between BSA12 and BSA16 is 72%.

The antibody or fragment thereof of the present invention may also comprise additional sequences to aid in expression, detection or purification of a recombinant antibody or fragment thereof. For example, and without wishing to be limiting, the antibody or fragment thereof may comprise a targeting or signal sequence (for example, but not limited to ompA), a detection tag (for example, but not limited to c-Myc, SEQ ID NO: 19), a purification tag (for example, but not limited to a histidine purification tag, SEQ ID NO: 20), or a combination thereof.

The antibody or fragment thereof of the present invention may also be in a multivalent display. Multimerization may be achieved by any suitable method of know in the art. For example, and without wishing to be limiting in any manner, multimerization may be achieved using self-assembly molecules[6,7], as described in WO2003/046560 (for example, but not limited to SEQ ID NO: 21). The described method produces pentabodies by expressing a fusion protein comprising the antibody or fragment thereof of the present invention and the pentamerization domain of the B-subunit of an $AB_5$ toxin family[8]; the pentamerization domain assembles into a pentamer, through which a multivalent display of the antibody or fragment thereof is formed. Each subunit of the pentamer may be the same or different. Additionally, the pentamerization domain may be linked to the antibody or antibody fragment using a linker; such a linker should be of sufficient length and appropriate composition to provide flexible attachment of the two molecules, but should not hamper the antigen-binding properties of the antibody. In one non-limiting example, the linker may be the linker of SEQ ID NO: 18.

In one, specific, non-limiting example, the antibody or fragment thereof of the present invention is provided in a pentabody, wherein at least one subunit may comprise a sequence selected from SEQ ID NO: 14, SEQ ID NO: 15, SEQ ID NO: 16, or a substantially identical sequence thereto.

Other forms of multivalent display are also encompassed by the present invention. For example, and without wishing to be limiting, the antibody or fragment thereof may be presented as a dimer, a trimer, or any other suitable oligomer. This may be achieved by methods known in the art, for example direct linking connection[9], c-jun/Fos interaction[10], "Knob into holes" interaction[11].

The antibody or fragment thereof of the present invention may have increased affinity for BSA. For example, and without wishing to be limiting in any manner, the antibody or fragment thereof may exhibit a binding affinity (expressed as dissociation constant, $K_D$ (Molar)) may be lower than about $10^{-6}$, $10^{-7}$, $10^{-8}$, $10^{-9}$, $10^{-10}$, or $10^{-11}$ M. In a non-limiting example, the $K_D$ may be lower than about $1 \times 10^{-7}$; alternatively, the $K_D$ may be between about $1 \times 10^{-7}$ and $4 \times 10^{-12}$ M, or between about $2.8 \times 10^{-7}$ and $4 \times 10^{-12}$ M. In another specific, but non-limiting example, the $K_D$ may be between about $3.6 \times 10^{-12}$ and $4 \times 10^{-12}$ M.

The present invention also encompasses nucleic acid sequences encoding the molecules as described herein. The nucleic acid sequence may be codon-optimized. The present invention also encompasses vectors comprising the nucleic acids as just described.

Furthermore, the invention encompasses cells comprising the nucleic acid and/or vector as described.

The present invention further encompasses the isolated or purified antibody or fragment of the present invention immobilized onto a surface. Immobilization of the antibody or fragment of the present invention may be useful in various applications for purifying or isolating proteins.

The surface is a microtiter plate, a sensorchip, or a resin bead. Solid surface may be any suitable surface, for example, but not limited to the well surface of a microtiter plate, channels of surface plasmon resonance (SPR) sensorchips, membranes, beads within a chromatography column, or any other useful surface.

The present invention will be further illustrated in the following examples. However, it is to be understood that these examples are for illustrative purposes only and should not be used to limit the scope of the present invention in any manner.

Example 1

Isolation of sdAbs Specific to BSA

A female llama was immunized with BSA. An sdAb phagemid display library was constructed from the VHH repertoire of this llama and this library was used for the isolation of sdAbs against BSA.

The llama immune phage display library was panned against 1 mg/ml BSA that was pre-adsorbed to a Reacti-Bind™ maleic anhydride activated microtiter plate well. About $10^{11}$ phage were added to the well and incubated at 37 C for 2 hr for antigen binding. After disposal of unattached phage, the wells were washed six times with phosphate buffered saline supplemented with 0.05% Tween 20 (PBST) for round one and washes were increased by one for each additional round. Phage were eluted by 10 min incubations with 100 µl 100 mM triethylamine and the eluate was subsequently neutralized with 200 µl 1M Tris-HCl (pH 7.5). Phage were rescued and amplified using M13KO7 (New England Biolabs, Mississauga ON) and used for the next round of panning. After three rounds of panning, eluted phage were used to infect exponentially growing E. coli TG1 (New England Biolabs, Mississauga ON) and rescued by M13KO7. The produced phage were used in phage ELISA.

For phage-ELISA, wells of a 96-well plate were coated overnight with 5 µg/ml BSA and then blocked with 1% casein for 2 hr at 37 C. Phage were pre-blocked with casein overnight, added to the preblocked wells and incubated for 1 hr. Positive phage clones detected by standard ELISA procedure, which revealed that 35 of the 38 analyzed phage clones bound to BSA.

These clones were sent for sequencing. Sequence analysis of these clones revealed four sdAbs: BSA7, BSA8, BSA12, and BSA16 (FIG. 1A).

Example 2

Construction, Expression, and Characterization of sdAbs

DNA encoding four sdAbs (BSA7, BSA8, BSA12, and BSA16; SEQ ID NO: 1-4, respectively) was amplified by PCR and flanked with BbsI and BamHI restriction sites. The products were cloned into the BbsI and BamHI sites of pSJF2H (kindly provided by J. Tanha, IBS, NRC) to generate pBSA7, pBSA8, pBSA12, and pBSA16.

All clones were inoculated in 25 ml LB-Ampicillin (30) and incubated at 37 C with 200 rpm shaking overnight. The next day, 20 ml of the culture was used to inoculate 1 L of M9 medium (0.2% glucose, 0.6% Na2HPO4, 0.3% KH2PO4, 0.1% NH4CL, 0.05% NaCl, 1 mM MgCl2, 0.1 mM CaCl2) supplemented with 0.4% casamino acids, 5 mg/l of vitamin B1 and 200 µg/ml of ampicillin, and cultured for 24 hr. Next, 100 ml of 10×TB nutrients (12% Tryptone, 24% yeast extract, and 4% glycerol), 2 ml of 100 mg/ml Amp and 1 ml of 1M isopropyl-beta-D-thiogalactopyranoside (IPTG) were added to the culture and incubation was continued for another 65-70 hrs at 28 C with 200 rppm shaking. E. coli cells were harvested by centrifugation and lysed with lysozyme. Cell lysates were centrifuged, and clear supernatant was loaded onto High-Trap™ chelating affinity columns (GE Healthcare, Uppsala, Sweden) and His-tagged proteins were purified.

The four sdAb genes were cloned into a periplasmic expression vector pSJF2H to generate sdAb expression vector (FIG. 1B), and the expressed protein was purified by immobilized metal affinity chromatography (IMAC). 3.1, 16.2 and 6.2 milligrams of protein was obtained from one liter of E. coli culture of pBSA8, pBSA12, and pBSA16 (FIG. 1C), respectively. Little protein was obtained from BSA7 expression, and further analysis of this protein was not conducted.

The purified proteins were dialyzed against HBS-E buffer. To assess formation of aggregates or lack thereof, size exclusion chromatography was carried out on BSA8, BSA12, and BSA16 with Superdex 75™ or Superdex 200™ column (Amersham Pharmacia, Piscataway, N.J.) in HBS as described previously (31). The elution volume of BSA8 (11.87 ml), BSA12 (111.72 ml) and BSA16 (11.80 ml) on a Superdex 75™ column suggested that all three proteins existed as monomers based on elution volumes of molecular weight markers run under the same conditions. No aggregation was observed from any of the three proteins.

Example 3

Affinity Measurement

The binding kinetics for the interactions of BSA8, BSA12, and BSA16 to immobilized BSA and other SA was determined by surface plasmon resonance (SPR) using BIACORE 3000 (GE Healthcare). 1700 RUs of BSA (Sigma) were immobilized on research grad CM5-sensorchip (BIACORE). Ethanolamin blocked surface was used as a reference. Immobilizations were carried out at the protein concentrations of 50 µg/ml in 10 mM acetate pH 4.5 using amin coupling kit supplied by the manufacturer. Antibodies were passed through Superdex 75™ (GE Healthcare) column to separate monomer prior to BIACORE analysis.

In all instances, analyses were carried out at 25 C in HBS-E buffer (10 mM HEPES, 150 mM NaCl, and 3 mM EDTA, pH 7.4) supplemented with 0.005% surfactant P20 at a flow rate of 20 µl/min. The surfaces were regenerated with 100 mM HCl (3 seconds). Data were analyzed with BIAevaluation 4.1 software.

Figure 2:
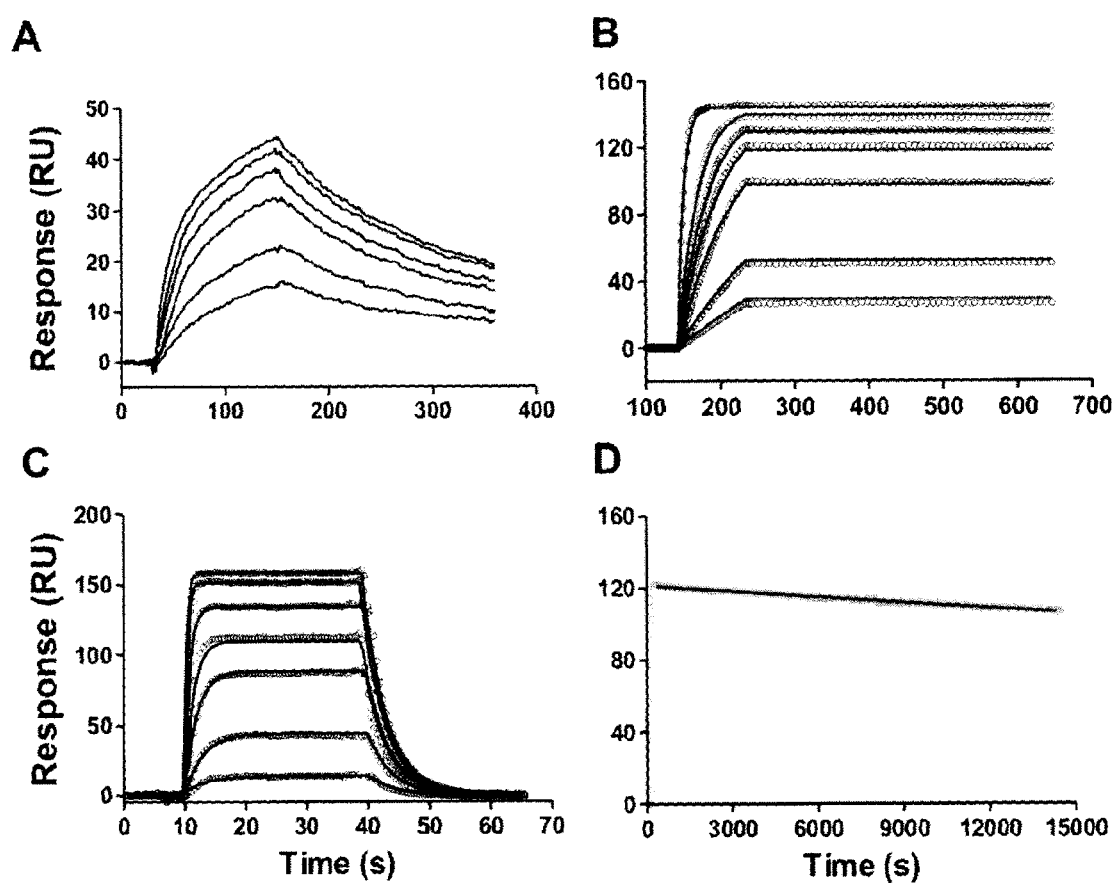
FIG. 2 shows interactions between BSA and the antibodies constructed in this work. (A) Binding of BSA8 to BSA at the concentrations of 10, 20, 40, 60, 80, and 100 nM. (B) Binding of BSA12 to BSA at the concentrations of 1, 2, 5, 10, 20, and 50 nM. (C) Binding of BSA16 to BSA at the concentrations of 25, 100, 300, 500, 1000, 2000, and 3000 nM. (D) Binding of BSA12 to BSA at 10 nM with extended dissociation time. Open circles are used for real data point and solid line for fitting of 1:1 binding model in B, C, and D where the fittings are reasonable good. (E) Bindings of 10 nM C3C-BSA8, C3C-BSA12, and C3C-BSA16 to BSA; (F) binding of 10 nM C3C-BSA8 to BSA; (G) binding of 1 µM BSA to C3C-BSA8, C3C-BSA12, and C3C BSA16 and (H) binding of 1.2 µM BSA to C3C-BSA8. (F) and (H) are to indicate interactions between C3C-BSA8 and BSA, which are invisible in (E) and (G) due to the scales used.
Figure 2:
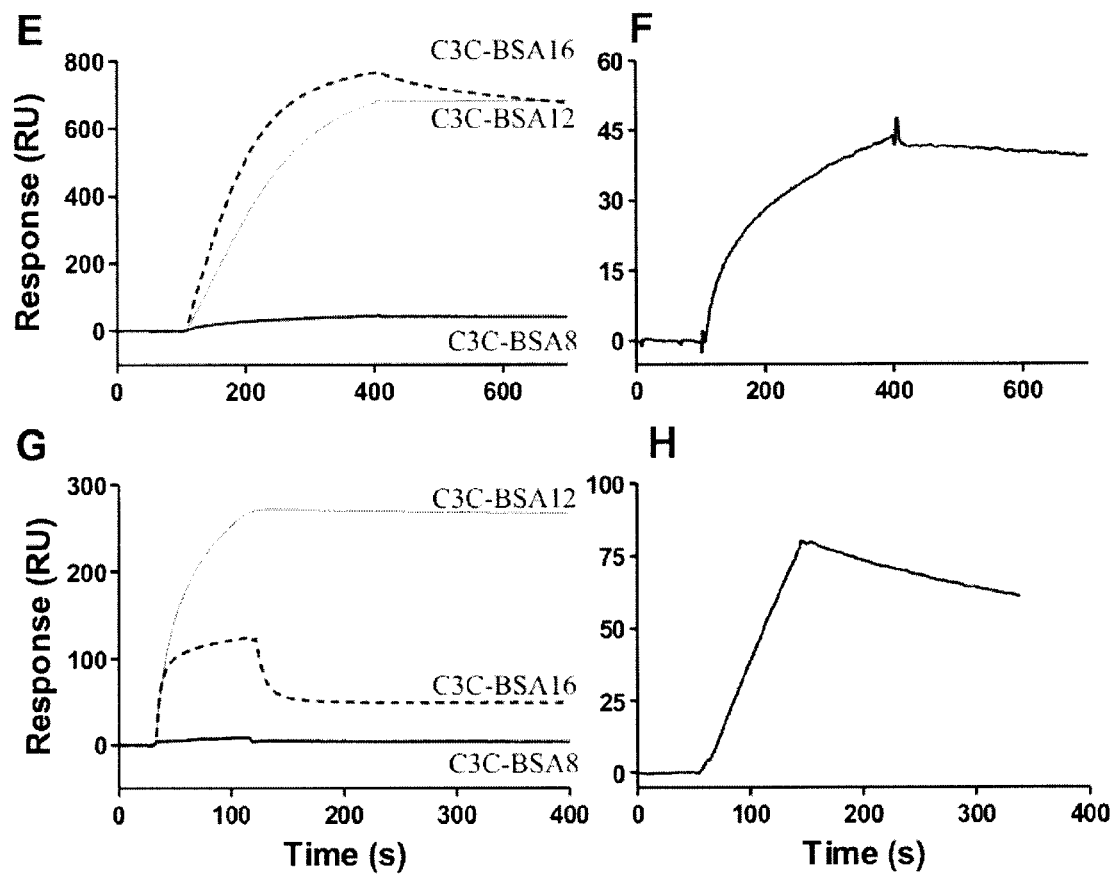

Affinities of the three sdAbs BSA8, BSA12, and BSA16 to BSA were determined by SPR with Biacore 3000. All three sdAbs bound to BSA specifically (FIG. 2). A higher binding capacity (~150 RU) was achieved by BSA12 (FIG. 2B) and BSA16 (FIG. 2C), whereas only about 40 RU of response was recorded for the binding of BSA8 to BSA (FIG. 2A). BSA8 showed binding to BSA with a dissociation rate (kd) of $5 \times 10^{-3}$ l/s and an estimated dissociation constant (KD) in the range of 100 nM. An accurate KD could not be determined because the SPR profiles did not fit to a 1:1 binding model (FIG. 2A).

BSA12 has an extremely tight binding to BSA (FIG. 2B). To measure an accurate affinity value, which requires longer dissociation time for very high affinity binders, dissociations was monitored again for 5 min at multiple concentrations from 1 to 50 nM and 4 hr at 10 nM (FIG. 2D). Each binding was performed three times, and the obtained data were reproducible. These experiments revealed a ka of $2.5 \times 10^6$ $M^{-1}s^{-1}$ and a kd of $1 \times 10^{-5}$ $s^{-1}$, giving a calculated KD of $4 \times 10^{-12}$ M (Table 1). Despite the extremely slow dissociation rate, the interaction fits nicely into a 1:1 binding model (FIG. 2D).

TABLE 1

Affinities of sdAbs to BSA

| | $k_a \pm$ SE (1/Ms) | $k_d \pm$ SE (1/s) | $K_D \pm$ SE (M) |
|---|---|---|---|
| BSA8 | NA | NA | $\sim 10^{-7}$ |
| BSA12 | $2.5 \times 10^6 \pm 3.2 \times 10^3$ | *$9 \times 10^{-6} \pm 3 \times 10^{-8}$ | $4 \times 10^{-12}$ |
| BSA16 | $1.0 \times 10^6 \pm 2.2 \times 10^4$ | $2.7 \times 10^{-1} \pm 5.4 \times 10^{-3}$ | $2.8 \times 10^{-7} \pm 1.1 \times 10^{-8}$ |

NA: data not analyzed
*kd was determined separately with 4 h dissociation time
ka = association rate constant;
kd = dissociation rate constant;
KD = dissociation constant;
SE = standard error;
s = second;
M = molar Example 4

Construction, Expression, and Characterization of Pentabodies

CTB-based pentabodies were constructed by standard molecular cloning procedures. DNA encoding CTB was amplified by PCR and flanked with BbsI restriction site and DNA encoding linker sequence GGGGSGGGGSGGGGS (SEQ ID NO: 18) at 5'- and 3'-ends, respectively. DNA encoding BSA8, BSA12, and BSA16 was amplified by PCR and flanked with DNA encoding the linker sequence GGGGSGGGGSGGGGS (SEQ ID NO: 18) and BamHI restriction site at 5'- and 3'-ends, respectively. CTB and the three sdAbs are fused at DNA level by overlap extension PCR. The final PCR product was digested by BbsI and BamHI and ligated into pSJF2 digested with the same enzymes to generate clones pC3C-BSA8, pC3C-BSA12, and pC3C-BSA16 (FIG. 1).

Expression of the three proteins were carried out as described in Example 3. CTB-based pentabodies were constructed by fusing each of the three isolated sdAbs BSA8, BSA12, and BSA16 to the C-terminus of CTB with a peptide linker GGGGSGGGGSGGGGS (SEQ ID NO: 18). The generated clines C3C-BSA8, C3C-BSA12, and C3C-BSA16 (FIG. 1B) have a subunit molecular weight of 28,257; 28,396; and 28,785 Dalton, respectively. The three proteins were expressed in E. coli and purified by IMAC (FIG. 1C). 10, 23 and 7 mgs of proteins were obtained from C3C-BSA8, C3C-BSA12, and C3C-BSA16, respectively.

Example 5

Affinities of the Pentabodies to the Target Antigen

SPR analysis was performed to assess the bindings of the three CTB-based pentabodies again. All three proteins showed specific binding to immobilized BSA (FIG. 2). Behaving similar to their monomeric counterparts, C3C-

BSA12 and C3C-BSA16 achieved high capacity bindings (~700RU, FIG. 2E) but C3C-BSA8 did not (~45RU, FIGS. 2E-F).

C3C-BSA12 showed the tightest binding to BSA with a $k_d$ slower than $10^{-6}$ 1/s. This is very close to the $k_d$ of BSA12, which is $9 \times 10^{-6}$ 1/s. This result showed that for an sdAb with very low $k_d$, pentamerization apparently did not increase its avidity. This is different from pentamerization of low affinity sdAbs, by which a very large gain in functional affinity can be achieved (see e.g. C3C-BSA8, and C3C-BSA16). Due to the multivalent nature of the bindings, an accurate kd of the bindings could not be calculated.

Figure 3:
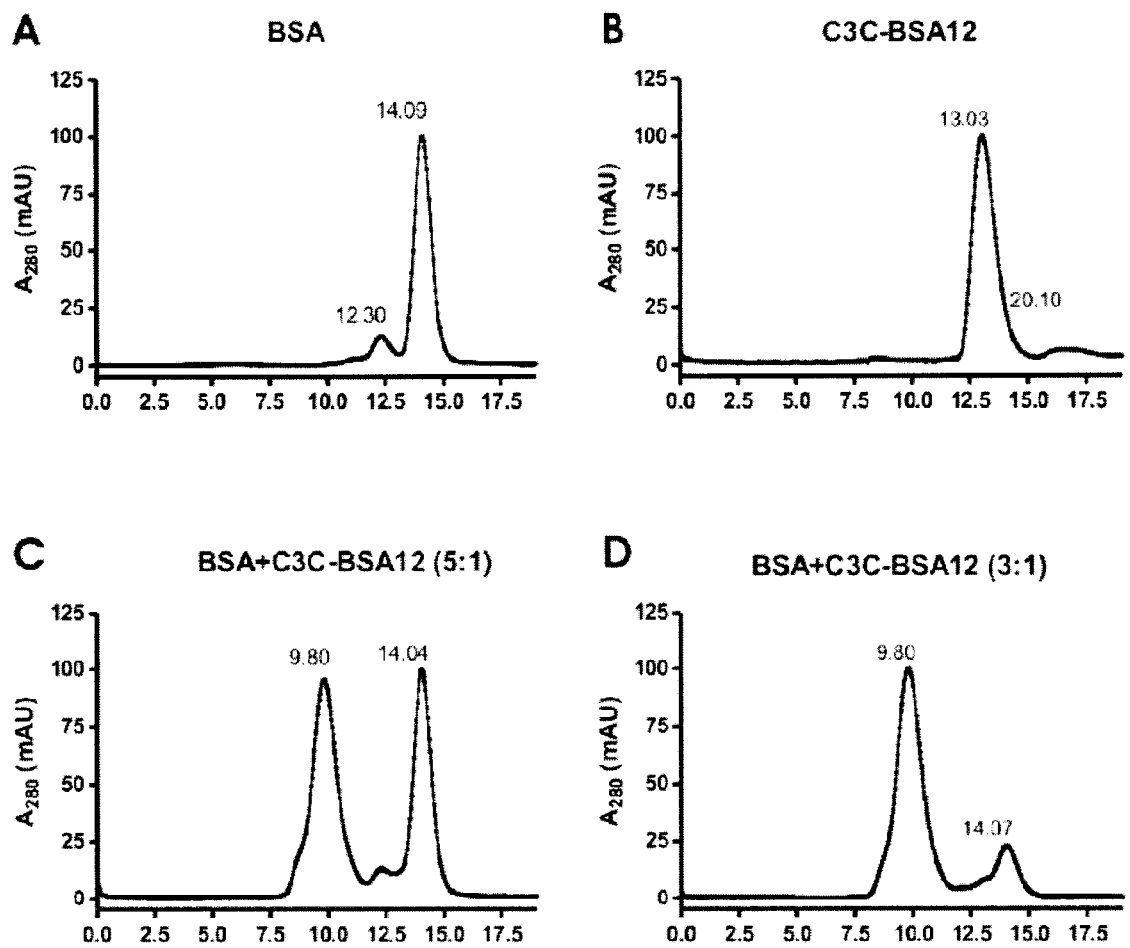
FIG. 3 shows the formation of protein complexes between the pentabodies and BSA. SEC profiles of BSA (A) and the pentabody C3C-BSA12 (B) on Superdex 200™ are shown at the top panel. Profiles of C3C-BSA8 and C3C-BSA16 are very similar to that of C3C-BSA12 and are not shown. (C) SEC profiles of a mixture of 80 µl 1 mg/ml BSA and 168 µl 1 mg-ml C3C BSA12 (molar ratio=5:1). Volume of C3C-BSA12 was adjusted to have a molar ratio of 3:1 (D), 2:1 (E), and 1:1 (F). Similarly, SEC profiles of mixtures of C3C-BSA16 and BSA (G) and C3C-BSA8 and BSA (H) at a molar ratio of 3:1 were shown. All graphs were normalized to 100 to facilitate comparison. C3C-BSA12, for example, is shown to form a tight complex.
Figure 3:
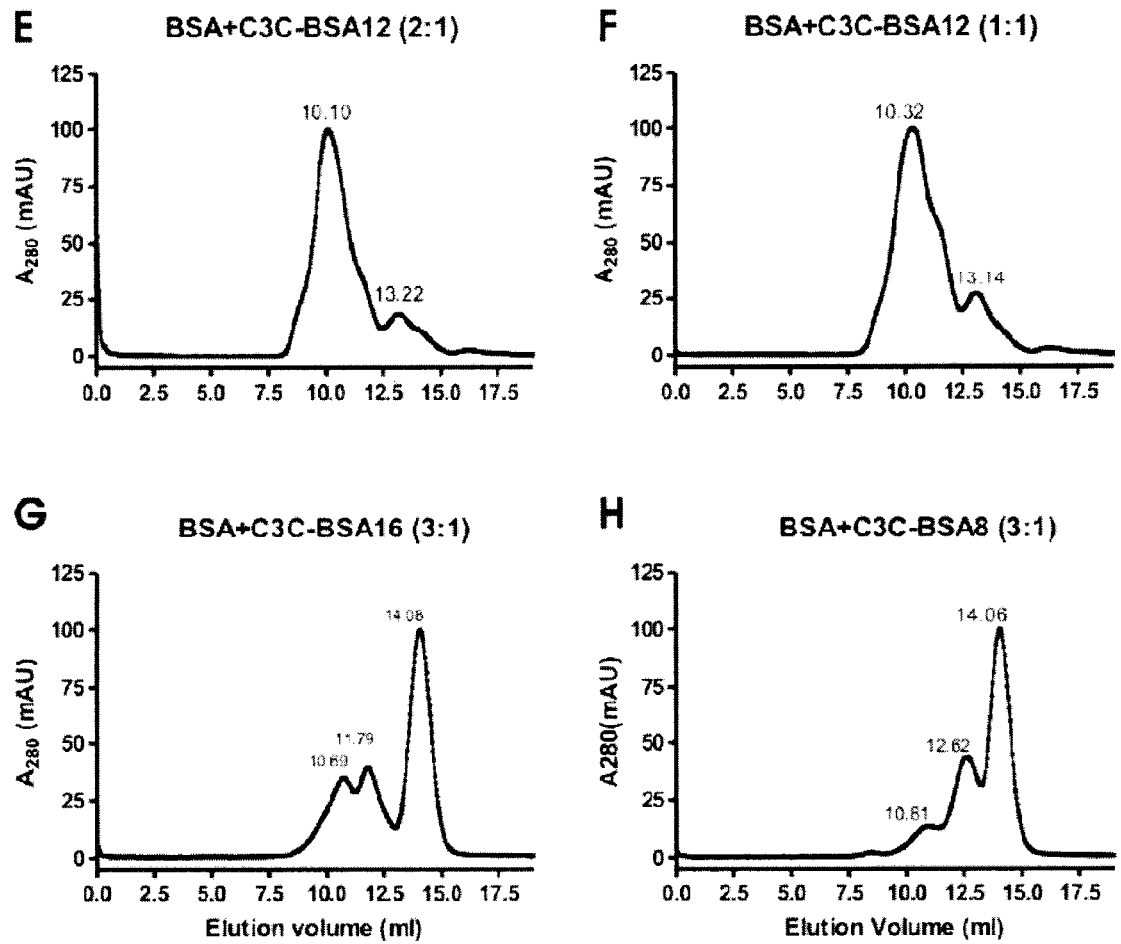

Binding of BSA to immobilized pentabodies (FIGS. 2G-H) revealed similar binding pattern as observed for monomeric bindings. However, dissociation rates were not calculated. A small portion of BSA exists in dimmer (FIG. 3A).

Example 6

Formation of BSA-Pentabody Complex

Formation of BSA-pentabody complex is important for the delivery of antigens through CTB-pentabodies, and this was tested with size exclusion chromatography (SEC). The three pentabodies and BSA were analyzed with SEC on a Superdex 200™ to determine their ability to form pentamer as CTB does. All three pentabodies were eluted at the volume of about 13 ml on a Superdex 200™ column (FIG. 3B, only the profile of C3C-BSA12 was shown as the three proteins have almost identical graphs). Based on molecular marker run under the same conditions, the actual MW of all three proteins were determined to be about 220 kDa. Although this number is between 7 to 8 times of their subunit MW, the three proteins are still considered pentamer based on the crystal structure of CTB.

No monomer was observed from all three proteins. The graphs also showed that the proteins form very little aggregations (FIG. 3B).

Monomeric BSA has a MW of 67 kDa, and a CTB-based pentabody has an estimated MW of about 143 kDa. BSA (FIG. 3A) and C3C-BSA12 (FIG. 3B) have a major elution peak at 14.09 and 13.03 ml when run on a Superdex 200™ column. When C3C-BSA12 and BSA were mixed at a 5:1 molar ratio, i.e., a 1:1 molar ration when BSA12 and BSA are concerned, a protein complex was formed (FIG. 3C, peak at 9.80 ml) but a large BSA peak was still visible. At a 3:1 pentabody BSA ratio (FIG. 3D), the BSA peak almost completely disappeared. This suggests that one C3C-BSA12 pentabody is able to carry approximately three BSA molecules. Further reduction of pentabody:BSA ratio to 2:1 (FIG. 3E) and 1:1 (FIG. 3F) resulted in a shift of the complex peak from 9.8 to 10.10 and 10.32 ml, respectively, probably caused by competition of BSA binding sites in a pentabody molecule by BSA.

C3C-BSA16 (FIG. 3G) and C3C-BSA8 (FIG. 3H) also form complex with BSA, But the height of the free BSA peaks at 14.08 ml suggests that the majority of the BSA remains unbound. In addition, the position of the protein complex peaks also suggest that association and dissociation between BSA and C3C-BSA16/C3C-BSA8 are constantly occurring. In conclusion, C3C-BSA12 is able to form tight protein complex with BSA whereas C3C-BSA8 and C3C-BSA16 did not.

Example 7

Affinities of BSA12 to Serum Albumins of Other Species

Affinities of BSA12 to serum albumins of various other species were determined as described in Example 3. Results are shown in Table 2.

TABLE 2

Affinity of BSA12 to serum albumins of various species

| Albumin | SI to BSA (%) | $k_a$ (1/Ms) | $k_d$ (1/s) | $K_D$ (M) |
|---|---|---|---|---|
| Bovine | 100 | $2.5 \times 10^6$ | $9 \times 10^{-6}$ | $3.6 \times 10^{-12}$ |
| Human | 77 | NA | NA | $1 \times 10^{-5} < K_D < 50 \times 10^{-5}$ |
| Murine | 70 | $2.7 \times 10^6$ | 0.16 | $5.9 \times 10^{-8}$ |
| Porcine | 80 | $6.8 \times 10^5$ | 0.22 | $3.8 \times 10^{-7}$ |
| Sheep | 92 | NA | NA | $1.0 \times 10^{-6}$ |
| Canine | 77 | NA | NA | $1.4 \times 10^{-6}$ |
| Goat | 92 | $1.2 \times 10^6$ | 0.3 | $2.4 \times 10^{-7}$ |
| Guinea pig | | $8.3 \times 10^5$ | 0.6 | $7.3 \times 10^{-7}$ |
| Rabbit | 72 | ND | ND | ND |
| Ovalbumin | 11 | ND | ND | ND |

NA: data not analyzable analyzable
NB: No binding was detected.

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

REFERENCES

All patents, patent applications and publications referred to throughout, as well as listed below, are hereby incorporated by reference in their entirety.

1. Padlan, E. A. Anatomy of the antibody molecule. *Molecular immunology* 31, 169-217 (1994).
2. Hamers-Casterman, C. et al. Naturally occurring antibodies devoid of light chains. *Nature* 363, 446-448 (1993).
3. Nuttall, S. D. et al. Isolation and characterization of an IgNAR variable domain specific for the human mitochondrial translocase receptor Tom70. *European journal of biochemistry/FEBS* 270, 3543-3554 (2003).
4. Jespers, L., Schon, O., Famm, K. & Winter, G. Aggregation-resistant domain antibodies selected on phage by heat denaturation. *Nat Biotechnol* 22, 1161-1165 (2004).
5. To, R. et al. Isolation of monomeric human V(H)s by a phage selection. *J Biol Chem* 280, 41395-41403 (2005).
6. Zhang, J. et al. A pentavalent single-domain antibody approach to tumor antigen discovery and the development of novel proteomics reagents. *J Mol Biol* 341, 161-169 (2004).
7. Zhang, J. et al. Pentamerization of single-domain antibodies from phage libraries: a novel strategy for the rapid generation of high-avidity antibody reagents. *J Mol Biol* 335, 49-56 (2004).
8. Merritt, E. A. & Hol, W. G. AB5 toxins. *Current opinion in structural biology* 5, 165-171 (1995).
9. Nielsen, U. B., Adams, G. P., Weiner, L. M. & Marks, J. D. Targeting of bivalent anti-ErbB2 diabody antibody fragments to tumor cells is independent of the intrinsic antibody affinity. *Cancer research* 60, 6434-6440 (2000).
10. de Kruif, J. & Logtenberg, T. Leucine zipper dimerized bivalent and bispecific scFv antibodies from a semi-synthetic antibody phage display library. *J Biol Chem* 271, 7630-7634 (1996).
11. Ridgway, J. B., Presta, L. G. & Carter, P. 'Knobs-into-holes' engineering of antibody CH3 domains for heavy chain heterodimerization. *Protein Eng* 9, 617-621 (1996).
PCT application No. PCT/CA02/01829

The invention claimed is:

1. An isolated or purified antibody or an antigen-binding fragment thereof, comprising the sequence of complementarity determining region (CDR) 1 selected from sequences NYTMA (SEQ ID NO:1), RYTIG (SEQ ID NO:2), and TWRMG (SEQ ID NO:3);

the sequence of CDR2 selected from sequences WSRGG-GATDYADSVKG (SEQ ID NO:4), RVNWSGGD-TYYADSVKG (SEQ ID NO:5), and AINLNTGN-TYYVDSVKG (SEQ ID NO:6); and the sequence of CDR3 selected from sequences GTDL-SYYYSTKKWAY (SEQ ID NO:7), SPK-WSEIPREYIY (SEQ ID NO:8), and RSPDSDYV-PLSSIDYQY (SEQ ID NO:9), wherein the isolated or purified antibody or antigen binding fragment thereof specifically binds bovine serum albumin.

2. The isolated or purified antibody or antigen-binding fragment thereof of claim 1, wherein the antibody is a single-domain antibody (sdAb).

3. The isolated or purified antibody or antigen-binding fragment thereof of claim 2, wherein the sdAb is of camelid origin.

4. The isolated or purified antibody or antigen-binding fragment thereof of claim 1, comprising the sequence:

(SEQ ID NO: 11)
QVKLEESGGGLAQAGGSLRLSCAASERTFIRYTIGWFRQAPGKEREFVG

RVNWSGGDTYYADSVKGRFTISRDNAKTTVTLQMSSLKPEDTAVYSCAA

SPKWSEIPREYIYWGPGTQVTVSS, or a sequence at least 95% identical thereto.

5. The isolated or purified antibody or antigen-binding fragment thereof of claim 1, comprising the sequence:

(SEQ ID NO: 12)
QVKLEESGGGLVQVGDSLRLSCAASGRTFSNYTMAWFRQFPGKEREFVA

VVSRGGGATDYADSVKGRFTISRDNAKNTMYLQMNSLKTDTAVYYCAAG

TDLSYYYSTKKWAYWGQGTQVTVSS, or a sequence at least 95% identical thereto.

6. The isolated or purified antibody or antigen-binding fragment thereof of claim 1, comprising the sequence:

(SEQ ID NO: 13)
QVKLEESGGGLVQAGGSLRLSCAPSGRTFRTWRMGWFRQAPGKEREFVA

AINLNTGNTYYVDSVKGRFTISGDYAKNTLYLQMNSLKPEDTAVYFCAA

RSPDSDYVPLSSIDYQYWGQGTQVTVSS, or a sequence at least 95% identical thereto.

7. The isolated or purified antibody or antigen-binding fragment thereof of claim 1, wherein the dissociation constant of the antibody or antigen binding fragment thereof to its ligand is lower than $10^{-6}$ M.

8. The isolated or purified antibody or antigen-binding fragment thereof of claim 1, wherein the dissociation constant of the antibody or antigen binding fragment thereof to its ligand is lower than $10^{-7}$ M.

9. The isolated or purified antibody or antigen-binding fragment thereof of claim 1, wherein the dissociation constant of the antibody or antigen binding fragment thereof to its ligand is lower than $10^{-11}$ M.

10. An antibody multivalent display comprising the isolated or purified antibody or antigen-binding fragment thereof of claim 1.

11. The antibody multivalent display of claim 10, wherein the antibody or antigen-binding fragment thereof is displayed in a pentamer.

12. The antibody multivalent display of claim 11, wherein at least one subunit of the pentamer comprises a sequence selected from SEQ ID NO:14, SEQ ID NO:15, SEQ ID NO:16 or a sequence at least 95% identical sequence thereto.

13. The isolated or purified antibody or antigen-binding fragment thereof of claim 1, wherein the antibody or antigen binding fragment thereof is immobilized onto a surface.

14. The isolated or purified antibody or antigen-binding fragment thereof of claim 13, wherein the surface is a microtiter plate, a sensorchip, or a chromatography resin.

* * * * *